(12) United States Patent
Prochiantz et al.

(10) Patent No.: US 8,575,105 B2
(45) Date of Patent: Nov. 5, 2013

(54) USE OF THE ENGRAILED HOMEODOMAIN PROTEIN AS ANXIOLYTIC

(75) Inventors: Alain Prochiantz, Paris (FR); Michel Volovitch, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 763 days.

(21) Appl. No.: 12/281,104

(22) PCT Filed: Feb. 28, 2007

(86) PCT No.: PCT/FR2007/000360
§ 371 (c)(1),
(2), (4) Date: Aug. 11, 2011

(87) PCT Pub. No.: WO2007/099227
PCT Pub. Date: Sep. 7, 2007

(65) Prior Publication Data
US 2011/0294739 A1    Dec. 1, 2011

(30) Foreign Application Priority Data

Feb. 28, 2006 (FR) ..................... 06 01749

(51) Int. Cl.
*A01N 37/18*    (2006.01)
(52) U.S. Cl.
USPC ................ 514/17.5; 514/17.6; 514/21.3

(58) Field of Classification Search
None
See application file for complete search history.

(56) References Cited

U.S. PATENT DOCUMENTS

| | | |
|---|---|---|
| 5,888,762 A | 3/1999 | Joliot |
| 6,080,724 A | 6/2000 | Chassaing |
| 2004/0029281 A1 | 2/2004 | Joliot |
| 2007/0054401 A1 | 3/2007 | Prochiantz |
| 2007/0155668 A1 | 7/2007 | Prochiantz |

FOREIGN PATENT DOCUMENTS

| | | |
|---|---|---|
| FR | 2 662 698 A | 12/1991 |
| FR | 2 855 178 A | 11/2004 |
| WO | WO 2005/007812 | 1/2005 |

OTHER PUBLICATIONS

Brunet et al., Nature, 2005, 438:94-8.*
Simon et al., J. Neurosci., 2001, 21(9):3126-31.*
Hanks et al., Science, 1995, 265:679-82.*
Sonnier et al. "Progressive loss of dopaminergic neurons in the ventral midbrain of adult mice hererozygote for Engrailed1." J. Neurosci. 27: 1063-1071, Jan. 31, 2007.

* cited by examiner

*Primary Examiner* — Olga N Chernyshev
(74) *Attorney, Agent, or Firm* — Morgan, Lewis & Bockius LLP

(57) ABSTRACT

The present invention relates to the use of an Engrailed transcription factor for producing a medicament for anxiolytic purposes.

4 Claims, 2 Drawing Sheets

USE OF THE ENGRAILED HOMEODOMAIN PROTEIN AS ANXIOLYTIC

Related Applications

The present application is a U.S. National Phase Application of International Application PCT/FR2007/000360, filed Feb. 28, 2007, which claims the benefit of France Application No. 06/01749, filed Feb. 28, 2006, all of which are herein incorporated by reference in their entirety.

The present invention relates to the use of Engrailed transcription factors for increasing dopaminergic metabolism, and notably as anxiolytics.

The Engrailed proteins are transcription factors in the homeodomain protein class. Mammals possess two Engrailed genes: Engrailed-1 and Engrailed-2; the two corresponding proteins, which have similar biological activity, will be designated collectively hereinafter with the general term Engrailed (EN).

In neonates and in adults, EN is expressed in the dopaminergic (DA) neurons of the substantia nigra (which degenerate in Parkinson's disease), in the cerebellar granule cells and in the dopaminergic mesencephalic nuclei, which play an important role in the regulation of mood and the establishment of addictive behaviors.

It has been shown (SIMON et al. J. Neurosci. 21 (9):3126-34, 2001) that loss of EN in the course of development is followed quite quickly by degeneration of the dopaminergic neurons, and that one of the transcription targets of EN is alpha-synuclein, for which a genetic link to certain hereditary forms of Parkinson's disease has been demonstrated (POLYMEROPOULOS et al., Science. 276, 2045-7, 1997), and which is said to constitute a negative regulator of dopaminergic transmission (ABELIOVICH et al., Neuron, 25, 239-52, 2000).

Together, these observations strongly suggest involvement of EN in neurodegenerative pathologies, and notably in pathologies affecting the dopaminergic neurons, such as Parkinson's disease. It has been proposed to regulate the activity of EN to prevent these pathologies or slow down their progression. Thus, PCT application WO 2004/104030 describes peptides that modulate the activity of Engrailed, and proposes their use for preventing or treating neurodegenerative pathologies.

The inventors have now discovered that in addition to its effects on neuron survival, EN also has a direct effect on dopaminergic metabolism.

They observed that the administration of Engrailed to mice induced in them an anxiolytic effect, which was accompanied by a considerable increase in the DOPAC/DA ratio, which reflects an increase in dopamine metabolism, in the striatum, as well as an increase in cortical serotonin.

Accordingly, the present invention relates to the use of an Engrailed protein for producing an anxiolytic medicinal product.

As pointed out above, "Engrailed protein" is used here to denote either of the proteins Engrailed-1 or Engrailed-2 of a vertebrate. Preferably, an Engrailed protein will be selected from the species to which the subject to be treated belongs.

Advantageously, said medicinal product is an injectable preparation, preferably by the intravenous route.

The present invention will be better understood from the rest of the description given below, which refers to examples illustrating the anxiolytic properties of Engrailed, and its effects on dopaminergic metabolism.

EXAMPLE 1

Figure 1:
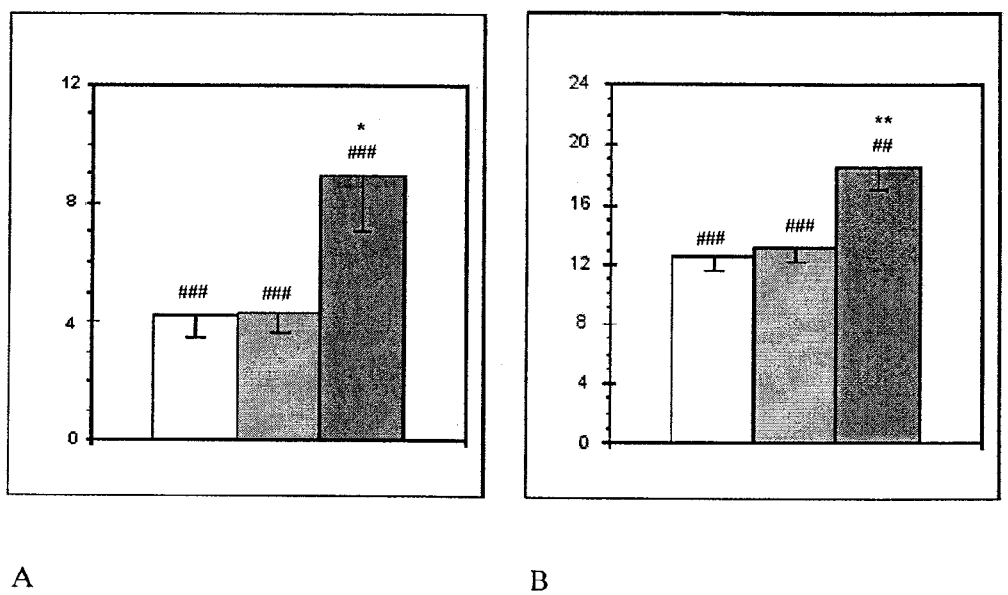
FIG. 1 depicts the percentage of time spent at the center (A), and the percentage of distance covered at the center (B), for the control mice (Sal; □), the mice that received an injection of 3 μg/kg (□), and the mice that received an injection of 300 μg/kg (■) of EN2. Difference vs. 25%: ## $p<0.01$; ### $p<0.001$.

The effects of a daily injection of EN2 at a dose of 3 or 300 μg/kg on the behavior of mice was evaluated as follows:

Subjects:

The tests were carried out on male Swiss mice, aged 6 months.

Preparation of Engrailed-2 for Injection:

The chicken EN2 protein (UniProtKB access number: Q05917) is produced in recombinant form in *E. coli* bacteria BL21RP-CodonPlus® (Stratagene) transformed with the plasmid pGEXSEn2, which results from insertion of the sequence coding for the whole of EN2 in a plasmid pGEX-6P (Amersham-GE Healthcare), in translational fusion with the sequence coding for glutathione S-transferase (GST).

The protein expressed is a fusion protein containing the sequence of glutathione S-transferase, followed by a cleavage site for the PreScission™ protease (recombinant protease resulting from fusion between GST and the protease 3C of the human rhinovirus; Amersham-GE Healthcare), and of the complete sequence of EN2.

This fusion protein is purified from a lysate of the transformed bacteria, by affinity chromatography on a glutathione column (GSTrap, Amersham-GE Healthcare); the EN2 protein is eluted from the column after cleavage using the PreScission™ protease.

Tests Performed

Y-maze: in this test, the animal is put in a Y-shaped maze. Each visit to one of the arms of the maze is noted, and the total number of visits in one or other arm, as well as their succession from one arm to the other, are recorded. The percentage of alternation between the arms makes it possible to evaluate working memory, the total number of visits to the arms permits evaluation of activity, and the development of this activity permits evaluation of short-term and long-term habituation.

Rotarod: the length of time that the animal is able to remain on a rotating cylinder is measured, which permits motor coordination and balance to be evaluated.

Tail-pinch: this test permits the pain threshold to be measured.

Open-field: the animal is put in a brightly lit enclosure, for a 30-minute session. The distance covered and the number of rearings permit evaluation of locomotor and exploratory activity; the variation of this activity between the first and the second half of the test permits evaluation of memory of the habituation type. Finally, determination of the time spent, and of the distance covered, at the center of the enclosure (which constitutes an anxiogenic environment) permits the level of anxiety to be evaluated.

The center of the open-field is defined as a square at the center of the enclosure representing 25% of the total area. The variables index of anxious type of behavior are the percentage of time spent and the percentage of distance covered at the center. The anxiogenic character of the center is indicated by avoidance behavior with respect to the center, therefore by values below 25% for these two variables. An anxiolytic type of effect of a treatment is manifested by an increase in the percentages of time spent and of distance covered at the center.

Elevated-plus maze: this is a cross-shaped device having 2 open arms and 2 arms closed at the sides. The animal is put in the maze for a 5-minute session. The total number of entries into the 2 types of arms is measured (exploratory activity in anxiogenic environment), as well as the percentage of entries into the open arms (the most anxiogenic), and the time spent in these arms. In the majority of cases, the mouse spends less than 50% of the time and effects less than 50% of the entries into the open arms, which attests to the anxiogenic character of the latter. Anxious type of behavior is therefore regarded as more pronounced when the percentages of time and of entries into the open arms are lower. The anxiolytic type of effect of a treatment is manifested by an increase in the percentages of time and of entries into the open arms.

Procedure:

The injections were performed according to the following protocol:

Twenty-one animals were divided at random into 4 groups, which received injections of:

NaCl 0.9%: control group (Sal); n=10);
EN2 3 µg/kg: group EN3 (n=10);
EN2 300 µg/kg: group EN300 (n=10).

The injections were performed intravenously in the tail. The timetable of the injections and of the tests is as follows:

| Day 1: | t = 0 | Injection 1 |
| --- | --- | --- |
| | t = 1 h | Y-maze - Session 1 |
| Day 2: | t = 0 | Injection 2 |
| | t = 1 h | Y-maze - Session 2 |
| | t = 1 h 40 | Rotarod - Session 1 |
| Day 3: | t = 0 | Injection 3 |
| | t = 1 h | Y-maze - Session 3 |
| | t = 1 h 40 | Rotarod - Session 2 |
| Day 4: | t = 0 | Injection 4 |
| | t = 1 h | Y-maze - Session 4 |
| | t = 1 h 40 | Rotarod - Session 3 |
| | t = 1 h 55 | Tail-pinch - Session 1 |
| Day 7: | t = 0 | Injection 5 |
| | t = 1 h | Open-Field |
| | t = 1 h 40 | Rotarod - Session 4 |
| | t = 1 h 55 | Tail Pinch - Session 2 |
| Day 8: | t = 0 | Injection 6 |
| | t = 1 h | Elevated-plus maze |

Results:

Locomotor Activity:

No notable effect of EN2 is found at 3 and 300 µg/kg—neither for the maze, nor for the Rotarod, nor for the tail-pinch test, nor in open-field. Therefore it is not possible to conclude that there is an effect of EN2 on locomotor and exploratory activity in the experimental conditions used.

Habituation Type of Memory:

Habituation to an environment is manifested by exploratory activity, which decreases when this environment becomes known. The habituation index variables are the horizontal and vertical activities, measured in the 2nd half of a session in open-field, and expressed as percentage of the activity for the whole session. Habituation is indicated by values for these two variables below 50%.

The percentage of distance at the center and of rearings in the 2nd half of the session is significantly less than 50% for the three groups. EN2 does not alter these two variables significantly. It is not possible to conclude that there is an effect of EN2 on memory of the habituation type in the experimental conditions used.

Anxiolytic Activity:

Open Field

The results are presented in FIG. 1, which shows the percentage of time spent at the center (A), and the percentage of distance covered at the center (B), for the control mice (Sal; □), the mice that received an injection of 3 µg/kg (□), and the mice that received an injection of 300 µg/kg (■) of EN2. Difference vs. 25%: ## p<0.01; ### p<0.001.

Difference vs. control group (Sal): *p<0.05; **p<0.01.

It can be seen that, for the 3 groups of animals, the percentages of time spent and of distance covered at the center are less than 25%, which shows avoidance of the center, indicating the anxiogenic character of the latter.

At a dose of 3 µg/kg, EN2 does not have a significant effect on the animals' behavior; in contrast, at a dose of 300 µg/kg, EN2 very significantly (p<0.01) increases the percentage of time spent and the percentage of distance covered at the center, which shows an anxiolytic type of effect.

Elevated-Plus Maze

Figure 2:
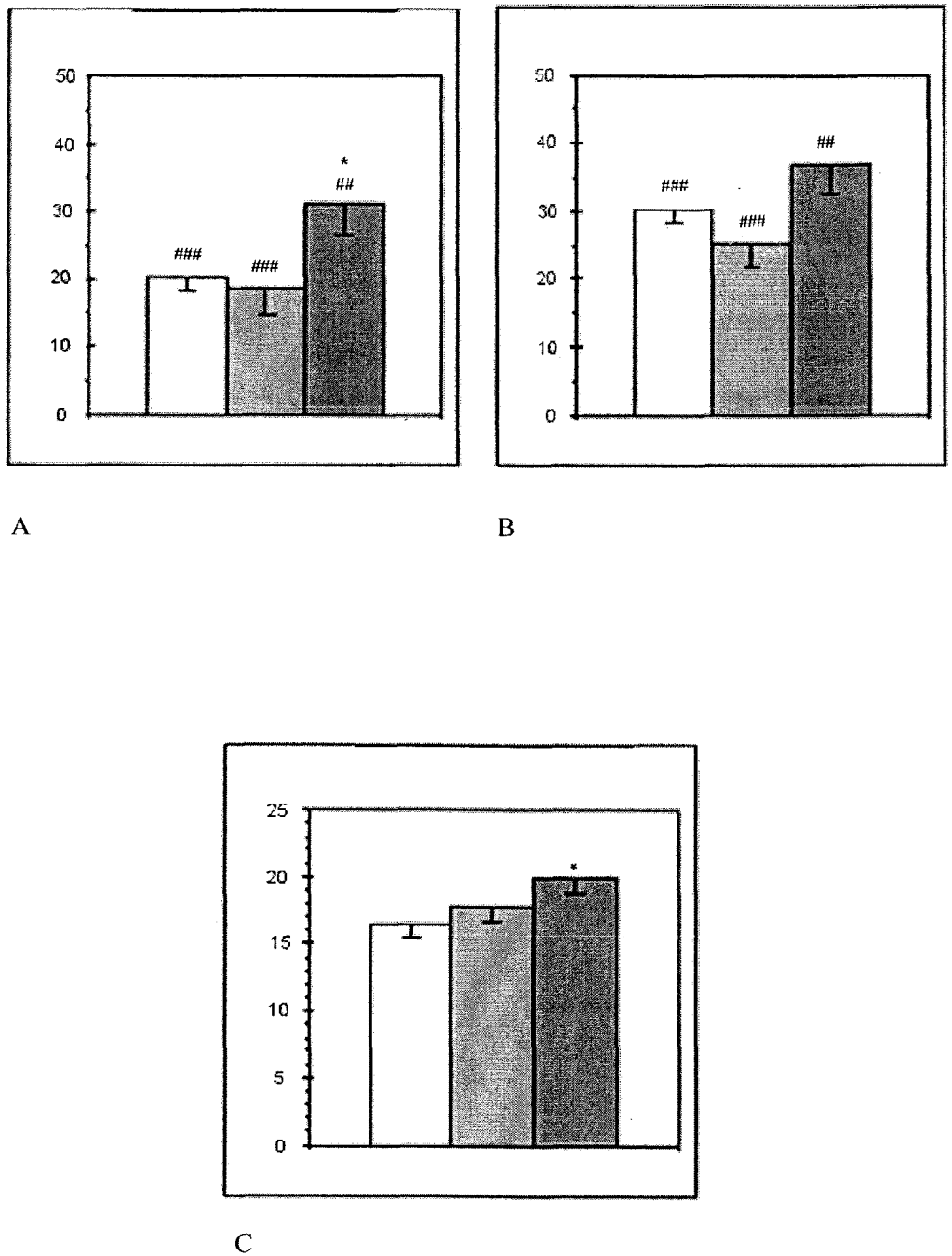
FIG. 2 depicts the total number of entries into the open or closed arms (A), the percentage of time in the open arms (B) and the percentage of entries into these arms (C), for the control mice (Sal; □), the mice that received an injection of 3 μg/kg (□) of EN2, and the mice that received an injection of 300 μg/kg (■) of EN2.

The results are presented in FIG. 2, which shows the total number of entries into the open or closed arms (A), the percentage of time in the open arms (B) and the percentage of entries into these arms (C), for the control mice (Sal; □), the mice that received an injection of 3 µg/kg (□) of EN2, and the mice that received an injection of 300 µg/kg (■) of EN2. Difference vs. 50%: ## p<0.01; ### p<0.001. Difference vs. control group (Sal): *p<0.05.

The three groups of animals show percentages of time and of entries into the open arms less than 50%, which indicates the anxiogenic character of the open arms.

At a dose of 3 µg/kg, EN2 does not have a significant effect on the animals' behavior.

At a dose of 300 µg/kg, EN2 increases the number of entries into the arms, open or closed, which suggests an increase in exploratory behavior and/or a decrease in anxiety, and also significantly increases the percentage of time spent in the open arms.

The results of these tests indicate that treatment with the EN2 protein induces an anxiolytic type of effect.

EXAMPLE 2

Effect of Engrailed-2 on Cerebral Amines

The day after the tests described in Example 1, the mice in the control group and in group EN300 received a 7th injection, respectively of NaCl 0.9% and of EN2 at a dose of 300 µg/kg.

One hour after the injection, the animals were sacrificed by decapitation. The brains were quickly removed and placed on a refrigerated plate (0-4° C.). The brain structures (cortex, striatum, and hippocampus) were dissected, weighed and put in an Eppendorf tube at −30° C. before preparation of the chromatography samples.

The tissues were homogenized with a teflon Potter in 500 µl of a solution of 0.1 N perchloric acid containing 0.05% of sodium metabisulfite. The samples were centrifuged (25000× g, 30 min, 4° C.). The supernatants were removed and then frozen before being chromatographed.

Dopamine (DA) as well as one of its metabolites, 3,4-dihydroxyphenylacetic acid (DOPAC), and serotonin, were determined in these supernatants by liquid chromatography combined with mass spectrometry (LC-MS).

The compounds were separated by reverse-phase partition chromatography, on a grafted silica C18 column; elution was performed with a Methanol/Water mixture: 15/85.

Detection was performed using an LCQ mass spectrometer (ThermoFinnigan). This comprises an ion trap equipped with a source of ionization of the Electrospray type operating in positive ionization mode.

The results are shown below in Tables I, II, and III.

TABLE I

| STRIATUM | DA (ng/mg tissue) | 5HT (ng/mg) | DOPAC (ng/mg) | DOPAC/DA |
|---|---|---|---|---|
| Control (10) | Moy 15.42 ESM 1.45 | Moy 1.42 ESM 0.29 | Moy 6.36 ESM 0.54 | Moy 0.41 ESM 0.03 |
| Treated (10) | Moy 14.08 ESM 1.70 ns | Moy 1.14 ESM 0.19 ns | Moy 8.33 ESM 1.15 p < 0.1 | Moy 0.62 ESM 0.08 p < 0.05 |

TABLE II

| CORTEX | DA (ng/mg tissue) | 5HT (ng/mg) | DOPAC (ng/mg) | DOPAC/DA |
|---|---|---|---|---|
| Control (10) | Moy 1.11 ESM 0.05 | Moy 2.42 ESM 0.21 | Moy 5.89 ESM 0.22 | Moy 5.57 ESM 0.35 |
| Treated (10) | Moy 1.25 ESM 0.08 ns | Moy 3.10 ESM 0.26 p < 0.1 | Moy 6.17 ESM 0.26 ns | Moy 4.97 ESM 0.49 ns |

TABLE III

| HIPPOCAMPUS | DA (ng/mg tissue) | 5HT (ng/mg) | DOPAC (ng/mg) | DOPAC/DA |
|---|---|---|---|---|
| Control (10) | Moy 0.12 ESM 0.01 | Moy 0.28 ESM 0.06 | Moy 0.51 ESM 0.06 | Moy 3.74 ESM 0.30 |
| Treated (10) | Moy 0.12 ESM 0.02 ns | Moy 0.28 ESM 0.06 ns | Moy 0.43 ESM 0.09 ns | Moy 3.93 ESM 0.24 ns |

We observe a slight increase in DOPAC and a marked increase (50% $p<0.05$) in the DOPAC/DA ratio in the striatum, as well as a slight increase in 5HT in the cortex.

The invention claimed is:

1. A method of inducing an anxiolytic effect in a subject in need thereof, comprising administering an Engrailed protein 2 to the subject in an amount sufficient to induce the anxiolytic effect in the subject.

2. The method according to claim 1, wherein the amount of the Engrailed protein is more than 3 µg/kg.

3. The method according to claim 1, wherein the amount of the Engrailed protein is 300 µg/kg.

4. The method according to claim 1, wherein the administration is by injection.

* * * * *